United States Patent
Wang et al.

(10) Patent No.: US 8,323,678 B2
(45) Date of Patent: Dec. 4, 2012

(54) IMPLANTABLE MEDICAL DEVICES COMPRISING POLY[L-LACTIDE-CO-(3,6-DIALKYL-1,4-DIOXANE-2,5-DIONE)]

(75) Inventors: Yunbing Wang, Sunnyvale, CA (US); Xiao Ma, San Jose, CA (US); Lothar Kleiner, Los Altos, CA (US); Thierry Glauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 231 days.

(21) Appl. No.: 12/770,591

(22) Filed: Apr. 29, 2010

(65) Prior Publication Data

US 2011/0270387 A1    Nov. 3, 2011

(51) Int. Cl.
*A61F 2/04* (2006.01)
(52) U.S. Cl. .................. 424/423; 623/23.7; 523/113
(58) Field of Classification Search .................. None
See application file for complete search history.

(56) References Cited

U.S. PATENT DOCUMENTS

| 3,636,956 | A | * | 1/1972 | Schneider | 606/224 |
| 6,730,772 | B2 | | 5/2004 | Shastri | |
| 2008/0243228 | A1 | * | 10/2008 | Wang et al. | 623/1.15 |

OTHER PUBLICATIONS

Yin (Synthesis and kinetic study of polylactide copolymers, 41 Polymer Preprints 184 (2000).*

* cited by examiner

*Primary Examiner* — Robert A Wax
*Assistant Examiner* — H. Sarah Park
(74) *Attorney, Agent, or Firm* — Squire Sanders (US) LLP

(57) ABSTRACT

This invention is directed to implantable medical device comprising a polymeric composition comprising poly[L-lactide-co-(3,6-dialkyl-1,4-dioxane-2,5-dione)], alone or as a blend with one or more polymers selected from the group consisting of poly(L-lactide) and poly(3,6-dialkyl-1,4-dioxane-2,5-dione).

17 Claims, No Drawings

IMPLANTABLE MEDICAL DEVICES COMPRISING POLY[L-LACTIDE-CO-(3,6-DIALKYL-1,4-DIOXANE-2,5-DIONE)]

FIELD

This invention relates to the fields of polymer chemistry, material science, medical devices and the treatment of vascular diseases.

BACKGROUND

In the field of implantable medical devices, polymers based on L-lactic acid are quite favored due to their excellent biocompatibility. That is, lactic acid polymers biodegrade to smaller fragments and eventually to small molecules including lactic acid itself, a naturally occurring compound in the mammalian system. Thus, the degradation products of polylactic acids tend to be generally well-tolerated by subjects.

When synthesizing poly(lactic acid) it is possible to use lactic acid itself as the monomer. The molecular weight of the polymer obtained, however is limited and if higher molecular weight product is desired, lactide, the dimer of lactic acid is the preferred monomer. For the purposes of this disclosure, poly(lactide) will be used to signify that the resultant polymers may have a broad range of molecular weights.

Constructs made of poly(lactide) exhibit good mechanical characteristics such as strength and tensile modulus. The fracture toughness of poly(lactide) is, however, lower than is often desired in a particular construct, for example in implantable medical devices such as stents. The high strength and tensile modulus and concomitant low fracture toughness stems from the high degree of crystallinity of poly(lactide), which is about 37%. In addition to the relatively high percent crystallinity, the crystalline structure of poly(lactic acid) in general comprises relatively large spherulites that add to the strength and tensile modulus of the polymer but detract from the fracture toughness.

What is needed is a lactide-based composition that can be fabricated into an implantable medical device that exhibits strength, a good tensile modulus and improved fracture toughness. The present invention provides such a composition and implantable medical devices fabricated of that composition.

SUMMARY

Thus, in one aspect, the present invention relates to an implantable medical device comprising a device body that is fabricated of a composition, coated with one or more layers of the composition, or both, the composition comprising poly[L-lactide-co-poly(3,6-dialkyl-1,4-dioxane-2,5-dione)], alone or as a blend with one or more polymers selected from the group consisting of poly(L-lactide) and poly(3,6-dialkyl-1,4-dioxane-2,5-dione), wherein the poly[L-lactide-co-(3,6-dialkyl-1,4-dioxane-2,5-dione)] is a random or a block copolymer; the alkyl groups of the poly[L-lactide-co-(3,6-dialkyl-1,4-dioxane-2,5-dione)] are the same; those like alkyl groups may be the same as or different from the alkyl groups of the poly(3,6-dialkyl-1,4-dioxane-2,5-dione), which alkyl groups are likewise the same; and the alkyl groups are selected from the group consisting of 2C-20C straight or branched chain alkyl and 3C-6C cycloalkyl.

In an aspect of this invention, the alkyl groups are selected from the group consisting of 2C-6C straight or branched chain alkyl.

In an aspect of this invention, the poly[L-lactide-co-(3,6-dialkyl-1,4-dioxane-2,5-dione)] is a random copolymer.

In an aspect of this invention, the poly[L-lactide-co-(3,6-dialkyl-1,4-dioxane-2,5-dione)] is a block copolymer.

In an aspect of this invention, the block copolymer is a diblock copolymer.

In an aspect of this invention, the block copolymer is a triblock copolymer in which poly(L-lactide) is the middle block.

In an aspect of this invention, one or more polymers of the composition is a star polymer.

In an aspect of this invention, the star polymer(s) is(are) independently regular or variegated.

In an aspect of this invention, the initiator(s) for star polymer synthesis are independently, selected from the group consisting of 1,3-dihydroxy-2-hydroxymethylpropane, pentaerythritol and cyclopropane-1,2,3,-tricarboxylic acid.

In an aspect of this invention, the implantable medical device comprises a composition comprising poly[L-lactide-co-(3,6-dialkyl-1,4-dioxane-2,5-dione)] block copolymer wherein the lactide-derived block(s) have a number average molecular weight of about 100 to 300 Kg/mol and the 3,6-dialkyl-1,4-dioxane-2,5-dione-derived block(s) have a number average molecular weight of about 10 to 30 Kg/mol.

In an aspect of this invention, the poly[L-lactide-co-(3,6-dialkyl-1,4-dioxane-2,5-dione)] has a number average molecular weight of about 110 to about 1,000 Kg/mol.

In an aspect of this invention, the implantable medical device comprises a composition comprising poly[L-lactide-co-(3,6-dialkyl-1,4-dioxane-2,5-dione)] random copolymer wherein the amount of 3,6-dialkyl-1,4-dioxane-2,5-dione-derived constitutional unit is less than or equal to about 10 mol %.

In an aspect of this invention, the implantable medical device of this invention comprises a composition that is a blend of poly(L-lactide) and poly[L-lactide-co-(3,6-dialkyl-1,4-dioxane-2,5-dione)] wherein the poly[L-lactide-co-(3,6-dialkyl-1,4-dioxane-2,5-dione)] consists of about 20 to about 50 mol % of 3,6-dialkyl-1,4-dioxane-2,5-dione-derived constitutional unit.

In an aspect of this invention, composition of which the device body is fabricated or with which it is coated comprises poly(L-lactide) and poly[L-lactide-co-(3,6-dialkyl-1,4-dioxane-2,5-dione)] wherein the poly(L-lactide) is about 50 to about 96 wt % of the composition and the poly[L-lactide-co-(3,6-dialkyl-1,4-dioxane-2,5-dione)] is about 4 to about 50 wt % of the composition.

In an aspect of this invention, the implantable medical device of this invention comprises a composition that is about 9 to about 20 wt % poly(3,6-dialkyl-1,4-dioxane-2,5-dione); about 75 to about 90 wt % poly(L-lactide); and about 1 to about 5 wt % poly[L-lactide-co-(3,6-dialkyl-1,4-dioxane-2,5-dione)] random copolymer wherein the poly[L-lactide-co-(3,6-dialkyl-1,4-dioxane-2,5-dione)] random copolymer is about 20 to 50 mol % 3,6-dialkyl-1,4-dioxane-2,5-dione-derived constitutional unit.

In an aspect of this invention, the device body is fabricated from the composition.

In an aspect of this invention, the preceding device body is coated with one or more layers, one or more of which comprises the composition.

In an aspect of this invention, one or more of the above layers comprises a therapeutic agent.

In an aspect of this invention, the device body is comprised of a different material than the composition.

In an aspect of this invention, the preceding device body is coated with one or more layers, one or more of which comprises the composition.

In an aspect of this invention, one or more of the above layers comprises a therapeutic agent.

In an aspect of this invention, the implantable medical device is a stent.

An aspect of this present invention relates to a composition comprising poly[L-lactide-co-(3,6-dialkyl-1,4-dioxane-2,5-dione)], alone or as a blend with one or more polymers selected from the group consisting of poly(L-lactide) and poly(3,6-dialkyl-1,4-dioxane-2,5-dione), wherein the poly[L-lactide-co-(3,6-dialkyl-1,4-dioxane-2,5-dione)] is a random or a block copolymer; the alkyl groups of the poly[L-lactide-co-(3,6-dialkyl-1,4-dioxane-2,5-dione)] are the same; those like alkyl groups may be the same as or different from the alkyl groups of the poly(3,6-dialkyl-1,4-dioxane-2,5-dione), which alkyl groups are likewise the same; and the alkyl groups are selected from the group consisting of 2C-20C straight or branched chain alkyl and 3C-6C cycloalkyl.

In an aspect of this invention, the alkyl groups are selected from the group consisting of 2C-6C straight or branched chain alkyl.

In an aspect of this invention, the poly[L-lactide-co-(3,6-dialkyl-1,4-dioxane-2,5-dione)] is a random copolymer.

In an aspect of this invention, the poly[L-lactide-co-(3,6-dialkyl-1,4-dioxane-2,5-dione)] is a block copolymer.

In an aspect of this invention, the block copolymer is a diblock copolymer.

In an aspect of this invention, the block copolymer is a triblock copolymer in which poly(L-lactide) is the middle block.

In an aspect of this invention, one or more of the polymers is a star polymer.

In an aspect of this invention, the star polymer(s) are independently regular or variegated.

In an aspect of this invention, the initiator of star polymer polymerization is, or are independently, selected from the group consisting of 1,3-dihydroxy-2-hydroxymethylpropane, pentaerythritol and cyclopropane-1,2,3-tricarboxylic acid.

In an aspect of this invention, the composition comprises poly[L-lactide-co-(3,6-dialkyl-1,4-dioxane-2,5-dione)] block copolymer wherein the lactide block(s) have a number average molecular weight of about 100 to 300 Kg/mol and the 3,6-dialkyl-1,4-dioxane-2,5-dione block(s) have a number average molecular weight of about 10 to 30 Kg/mol.

In an aspect of this invention, the poly[L-lactide-co-(3,6-dialkyl-1,4-dioxane-2,5-dione)] has a number average molecular weight of about 110 to about 1,000 Kg/mol.

In an aspect of this invention, the composition comprises poly[L-lactide-co-(3,6-dialkyl-1,4dioxane-2,5-dione)] random copolymer wherein the amount of (3,6-dialkyl-1,4-dioxane-2,5-dione)-derived constitutional unit is less than or equal to 10 mol %.

In an aspect of this invention, the composition of this invention comprises a blend of poly(L-lactide) and poly[L-lactide-co-(3,6-dialkyl-1,4-dioxane-2,5-dione)] wherein the poly[L-lactide-co-(3,6-dialkyl-1,4-dioxane-2,5-dione)] comprises about 20 to about 50 mol % 3,6-dialkyl-1,4-dioxane-2,5-dione-derived constitutional unit.

In an aspect of this invention, the composition of this invention comprises poly(L-lactide) and poly[L-lactide-co-(3,6-dialkyl-1,4-dioxane-2,5-dione)] wherein the poly(L-lactide) is about 50 to about 96 wt % of the composition blend and the poly[L-lactide-co-(3,6-dialkyl-1,4-dioxane-2,5-dione)] is about 4 to about 50 wt % of the composition blend.

In an aspect of this invention, the composition comprises about 9 to about 20 wt % poly(3,6-dialkyl-1,4-dioxane-2,5-dione); about 75 to about 90 wt % poly(L-lactide); and about 1 to about 5 wt % poly[L-lactide-co-poly(3,6-dialkyl-1,4-dioxane-2,5-dione)] random copolymer wherein the poly[L-lactide-co-poly(3,6-dialkyl-1,4-dioxane-2,5-dione)] random copolymer is about 20 to 50 mol % (3,6-dialkyl-1,4-dioxane-2,5-dione).

DETAILED DESCRIPTION

It is understood that use of the singular throughout this application including the claims includes the plural and vice versa unless expressly stated otherwise. That is, "a" and "the" are to be construed as referring to one or more of whatever the word modifies. Non-limiting examples are: "a layer," or "the layer," which is understood to include one such layer, two such layers or even more such layers unless it is expressly stated or is unambiguously obvious from the context that such is not intended. Likewise, without limitation, "a polymer" or "the polymer" refers to a single polymer or a mixture of two or more polymers unless, again, it is expressly stated or absolutely obvious from the context that such is not intended. The converse is also to be taken as true, that is, reference to an item in the plural includes the singular unless it is otherwise unambiguously clear from the context that only the plural is intended.

As used herein, words of approximation such as, without limitation, "about" "substantially," "essentially" and "approximately" mean that the word or phrase modified by the term need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by ±15%.

As used herein, the use of "preferred," "preferably," or "more preferred," and the like refers to preferences as they existed at the time of filing of the patent application.

As used herein, an "implantable medical device" refers to any type of appliance that is totally or partly introduced, surgically or medically, into a patient's body or by medical intervention into a natural orifice, and which is intended to remain there after completion of the procedure. The duration of implantation may be essentially permanent, i.e., intended to remain in place for the remaining lifespan of the patient; until the device biodegrades and naturally disappears; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts.

As used herein, "device body" refers to a fully formed implantable medical device with an outer surface to which no coating or layer of material different from that of which the device itself is fabricated has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of, in particular with regard to this invention, to implantable medical devices fabricated from polymers including, without limitation, the polymeric compositions of this invention.

Presently preferred implantable medical devices of this invention are stents. A stent refers generally to any device used to hold tissue in place in a patient's body. Particularly useful stents, however, are those used for the maintenance of patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, the neuro, carotid, coronary, pulmonary, aorta, renal, biliary, iliac, femoral and popliteal, as well as other peripheral, vasculatures. A stent can be used for the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable.

As used herein, "optional" means that the element modified by the term may, but is not required to, be present.

As use herein, a "coating" or any form of the verb "to coat" refers to one or more layers of material substantially in sequential contact with one another disposed over the surface of a device body. "Layers" are simply relatively thin, sheet-like constructs of whatever material they are made of such as, without limitation, the compositions of this invention.

As used herein, a "composition" refers to a substantially homogenous mixture or blend (the terms being, for the purposes of this invention interchangeable) of primarily polymeric materials but with allowance for some additional materials such as plasticizers and other additives and/or excipients that might be expected to be found in an essentially polymeric mixture. By "substantially homogeneous" is meant that a sample taken from any location in the composition mass would have the same chemical make-up and the same weight percent of each chemical present as a sample taken from any other location in the composition mass but allowing for some variation from exact duplication due to the vagaries of mixing, sampling, analytic procedures, etc.

As used herein, a "primer layer" refers to a coating consisting of a polymer or blend of polymers that exhibit good adhesion characteristics with regard to the material of which the device body is fabricated and good adhesion characteristics with regard to whatever material is to be disposed over a surface of the device body. Thus, a primer layer serves as an intermediary layer between a device body and materials to be affixed to the device body and is, therefore, applied directly to the device body. Examples without limitation, of primers include acrylate and methacrylate polymers, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), parylene-C and, of course, the compositions of this invention.

As use herein, a layer that is "disposed over" an indicated substrate, e.g., without limitation, a device body or another layer, refers to a relatively thin, sheet-like coating of the material applied directly to essentially the entire exposed surface of the indicated substrate. By "exposed surface" is meant any surface regardless of its physical location with respect to the configuration of the device that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. The drug reservoir layer may also act as a rate-controlling layer. As used herein, "rate-controlling layer" refers to a polymer layer that controls the rate of release of therapeutic agents or drugs into the environment. The compositions of the present invention may function as a drug reservoir layer and also as a rate-controlling layer.

A rate-controlling layer, as noted above, refers to a layer of material that affects the rate of release of a therapeutic agent(s) contained in layers below it into the external environment. The compositions of this invention may also function as a separate rate-controlling layer as well as a drug reservoir layer or combination drug reservoir/rate-controlling layer.

As used herein, a "topcoat layer" refers to an outermost layer, that is, a layer that is in contact with the external environment and that is coated over all or substantially all other layers. The topcoat layer may be applied to provide, or provide additional, control of the rate of release of the therapeutic agent from the underlying reservoir layer, to confer better hydrophilicity on the device, to make the device more biocompatible, to better lubricate the device or merely as a physical protectant of the underlying layers. The topcoat layer, however, may also contain therapeutic agents, in particular if the treatment protocol being employed calls for essentially immediate release of one or more therapeutic agent (these being included in the topcoat layer) followed by the controlled release of another therapeutic agent or agents over a longer period of time. In some embodiments a composition of this invention may function as a topcoat layer.

A polymer of a composition of this invention may be a homopolymer, a copolymer, which may be an alternating or random copolymer or a block copolymer, or it may be a star polymer.

A homopolymer refers to a polymer comprising a single monomer, a monomer simply being a molecule that is iteratively reacted with itself to form chains of constitutional units, i.e., to form a homopolymer. A copolymer refers to a polymer prepared from two or more monomers that may be reacted so as to form a random copolymer, a regular alternating copolymer, a block copolymer or a star copolymer. A random copolymer has the general structure, assuming two monomers/constitutional units, x-x-y-x-y-y-y-x-y-y-x-x-x- . . . , while a regular alternating copolymer has the general structure: . . . x-y-x-y-x-y- . . . , it being understood that the juxtaposition of constitutional units shown is for purpose of illustration only and a copolymer of this invention may vary from that shown. A block copolymer has the general structure: . . . x-x-x-y-y-y-x-x-x-y-y-y- . . . Similarly to random and alternating copolymers, the number of constitutional units in each block and the number of blocks in a block copolymer of this invention are not in any manner limited by the preceding illustrative generic structure.

A block copolymer may be further designated as a diblock, triblock, tetrablock or, for any polymer consisting of more than two blocks, simply a "multi-block" copolymer, which, as should be apparent, simply refers to the number of discrete blocks identifiable in the polymer. For example, without limitation, the illustrative block copolymer shown in the above paragraph would be designated, insofar as the structure presented is concerned, a tetra- or multi- block copolymer.

A "star" polymer or copolymer refers to the product of the reaction of a small multifunctional core molecule with one or more difunctional molecules to create a branched configuration:

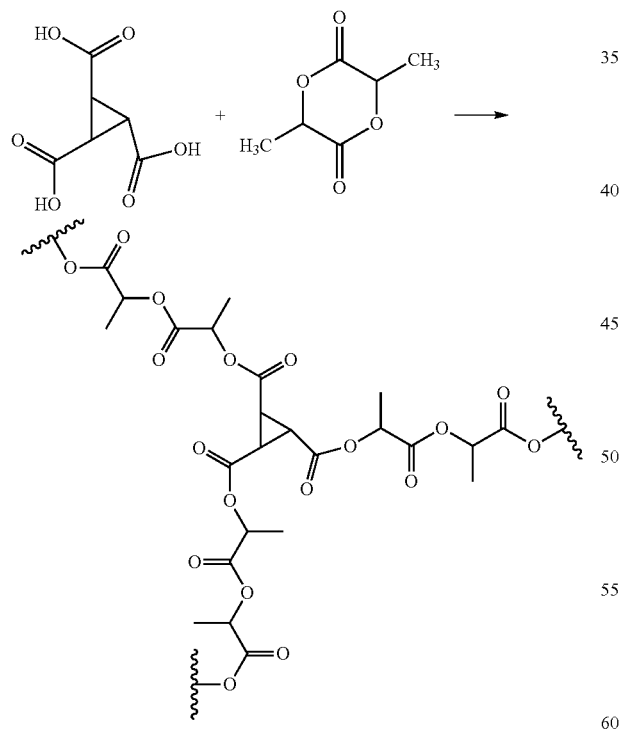

Any polymerization-initiating multifunctional group presently known as or may become known in the future may be used to synthesize a star polymer useful in the present invention. Presently preferred such groups include 1,3-dihydroxy-2-hydroxymethylpropane, pentaerythritol and cyclopropane-1,2,3-tricarboxylic acid.

A star polymer may be a homopolymer or a copolymer. It may also be a "regular" star or "variegated" star, the former referring to a star polymer in which the composition of each "arm" of the polymer is the same, i.e., is composed of the same constitutional units derived from the same monomers, while the latter refers to a polymer in which the compositions of the arms differ, i.e., are composed of different constitutional units derived from different monomers.

Implantable medical devices fabricated of poly(L-lactide) have been known for some time. However, they tend to display less than desirable fracture toughness. That fracture toughness can be improved using the compositions of this invention. Thus, presently preferred monomers for use in preparation of polymers of the compositions of this invention include L-lactide, D-lactide, meso-lactide and 3,6-dialkyl-1,4-dioxane-2,5-dione. L- and D-lactides, refer, of course, to the substantially enantiomerically pure monomers, those based on L- or D-lactic acid. Mesolactide refers to a lactide monomer in which one of the lactic acid moieties is L and the other is D. Presently preferred are L-lactide and 3,6-dialkyl-1,4-dioxane-2,5-dione. Homopolymers and copolymers of L-lactide and 3,6-dialkyl-1,4-dioxane-2,5-dione are biodegradable. "Biodegradable" refers to the property of a substance that decomposes or disintegrates when exposed to physiological conditions existing within the mammalian body such as pH, temperature, enzymes, metabolic processes, etc. and is thereupon absorbed by or eliminated from the body.

As used herein a "constitutional unit" refers to the repeating structure in a polymer backbone, the constitutional unit resulting from the reaction of monomers. For example, without limitation, poly(L-lactide), which is one of the presently preferred homopolymers of this invention, is prepared by the polymerization of the monomer L-lactide:

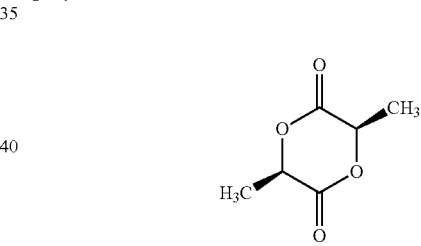

while the constitutional unit derived therefrom is

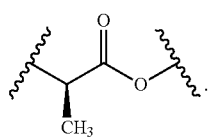

3,6-Dialkyl-1,4-dioxane-2,5-dione refers to the monomer of the formula:

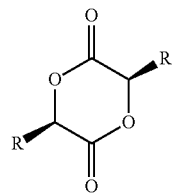

wherein R is an alkyl group.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —$CH_2$—, ethylene, —$CH_2CH_2$—, propylene, —$CH_2CH_2CH_2$—, n-butylene, —$CH_2CH_2CH_2CH_2$—, sec-butylene, —$CH_2CH_2CH(CH_3)$— and the like.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 20 carbon atoms that is m may be 1 and n may be 20. Of course, a particular alkyl group may be more limited, for instance without limitation, to 3 to 8 carbon atoms, in which case it would be designate as a (3C-8C)alkyl group. The numbers are inclusive and incorporate all straight or branched chain structures having the indicated number of carbon atoms. For example without limitation, a "$C_1$ to $C_4$ alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$— and $(CH_3)_3CH$—.

As use herein, a cycloalkyl group refers to an alkyl group in which the end carbon atoms of the alkyl chain are covalently bonded to one another. The numbers "m" to "n" then refer to the number of carbon atoms in the ring so formed. Thus for instance, a (3C-8C)cycloalkyl group refers to a three, four, five, six, seven or eight member ring, that is, cyclopropane, cyclobutane, cyclopentane, cyclohexane, cycloheptane and cyclooctane.

For the purposes of this invention, whenever the composition of a specific polymer is given, i.e., the weight percent of each constitutional unit of a polymer, such weight percent refers to the weight percent as calculated based on the molecular weight of the individual constitutional units as they appear in the actual polymer and not on the weight percent of each monomer that was reacted to yield the polymer.

Of course, if the weight percent refers to the amount of the whole polymer in a composition mixture or blend, it means simply the weight percent of that whole polymer calculated as the weight of the mass of that polymer in the blend divided by the weight of the entire mass of the composition.

Mol % refers to the number of moles of each constitutional unit in a copolymer divided by the total number of moles of all constitutional units in the copolymer. For example, without limitation, a copolymer comprising L-lactide-derived constitutional units and 3,6-Dialkyl-1,4-dioxane-2,5-dione-derived constitutional units and that is stated to be 10 mol % 3,6-Dialkyl-1,4-dioxane-2,5-dione means that if the number of moles of 3,6-Dialkyl-1,4-dioxane-2,5-dione-derived constitutional units and the number of moles of L-lactide-derived constitution units in a representative molecule of the polymer is determined and the number of moles of 3,6-Dialkyl-1,4-dioxane-2,5-dione-derived constitutional units is divided by the total number of moles of 3,6-Dialkyl-1,4-dioxane-2,5-dione-based constitutional units and L-lactide-based constitutional units in the molecules, the result will be the mol % of 3,6-Dialkyl-1,4-dioxane-2,5-dione-derived constitutional unit.

The average molecular weight of a polymer of this invention refers to the "number average molecular weight," which is calculated by dividing the weight of a sample of polymer by the total number of polymer molecules making up that sample.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a reduced level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, "treating" refers to the administration of a therapeutically effective amount of a therapeutic agent to a patient known or suspected to be afflicted with a vascular disease.

As used herein, a "patient" refers to any living organism that might benefit from the application of the implantable medical device and compositions of this invention. Preferable the patient is a mammal and most preferably at present the patient is a human being.

A "therapeutically effective amount" refers to that amount of a therapeutic agent that will have a beneficial affect, which may be curative or palliative, on the health and well-being of the patient with regard to the vascular disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery, or loss of organ function if the artery is peripheral.

"Restenosis" refers to the re-narrowing or blockage of an artery at or near the site where angioplasty or another surgical procedure was previously performed to remove a stenosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to smooth muscle cell proliferation. There were also issues of acute re-closure due to vasospasm, dissection, and thrombosis at the site of the procedure. Stents eliminated acute closure from vasospasm and greatly reduced complications from dissections. The use of IIb-IIIa anti-platelet drugs such as abciximab and epifabatide, which are anti-thrombotic, reduced the occurrence of post-procedure clotting (although stent placement itself can initiate thrombosis). Stent placement sites are also susceptible to restenosis due to abnormal tissue growth at the site of implantation. This form of restenosis tends also to occur at 3 to 6 months after stent placement and it is not affected by the use of anti-clotting drugs. Thus, alternative therapies are continuously being sought to mitigate, preferably eliminate, this type of restenosis. Drug eluting stents (DES), such as those of the instant invention, which release a variety of therapeutic agents at the site of stent placement, have been in use for some time and, as is the case with the invention herein, are being constantly improved.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth within the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, the reduced concentration of which, combined with macrophage-derived enzyme degradation, can cause the fibrous cap of these lesions to rupture unpredictably. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of relatively innocuous movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

"Thrombosis" refers to the formation or presence of a blood clot (thrombus) inside a blood vessel or chamber of the heart. A blood clot that breaks off and travels to another part of the body is called an embolus. If a clot blocks a blood vessel that supplied blood to the heart, it causes a heart attack. If a clot blocks a blood vessel that supplied blood to the brain, it causes a stroke.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to, without limitation, the kidneys, stomach, arms, legs and feet. In particular at present a peripheral vascular disease refers to a vascular disease of the superficial femoral artery.

Therapeutic agents that may be of use for the treatment of vascular disease using the compositions of this invention include, without limitation, antiproliferative agents, anti-inflammatory agents, antineoplastics and/or antimitotics, anti-platelet, anticoagulant, antifibrin, and antithrombin drugs, cytostatic or antiproliferative agents, antibiotics, antiallergic agents and antioxidants.

Suitable antiproliferative agents include, without limitation, actinomycin D, taxol, docetaxel, paclitaxel, FKBP-12 mediated mTOR inhibitors, perfenidone and prodrugs, co-drugs and combinations thereof.

Suitable anti-inflammatory agents include, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus and prodrugs, co-drugs and combinations thereof.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers (such as nifedipine), colchicine, fish oil (omega 3-fatty acid), histamine antagonists, lovastatin, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol and combinations thereof.

Suitable cytostatic (antiproliferative) agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Other suitable therapeutic agents include, without limitation, alpha-interferon, genetically engineered epithelial cells, DNA and RNA nucleic acid sequences, antisense molecules, ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides; antiviral agents; analgesics; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers, beta-blockers such as pindolol, antiarrhythmics; antihypertensives; diuretics; vasodilators including general coronary; peripheral and cerebral; central nervous system stimulants; hypnotics; immunosuppressives; muscle relaxants; parasympatholytics; psychostimulants; sedatives; tranquilizers and natural or genetically engineered lipoproteins.

EXAMPLES

Example 1

P[L-lactide-co-(3,6-di-(n-butyl)-1,4-dioxane-2,5-dione)] Block Copolymer

A 3 liter reactor equipped with a mechanical stirrer is placed in a glove box, which is then purged with nitrogen. The reactor is preheated to remove any residual moisture. L-lactide (400 g), 0.44 mL dodecanol (initiator), 1 L toluene and 1.2 mL stannous octoate are charged to the reactor and the mixture is heated to 120° C. with stirring and held there for 24 hrs. 3,6-Di-(n-butyl)-1,4-dioxane-2,5-dione (40 g) is then added to the reactor and the solution stirred at 120° C. for another 24 hrs. The reaction mixture is cooled and one liter of chloroform is added to the reactor to dilute the solution. The solution is then poured into 6 L of methanol wherein the product precipitates. The product is filtered, washed with methanol and dried at 80° C. under vacuum to a constant weight.

Example 2

Poly[L-lactide-co-(3,6-di-(n-butyl)-1,4-dioxane-2,5-dione)] Random Copolymer

A 3 liter reactor equipped with a mechanical stirrer is placed in a glove box, which is then purged with nitrogen. The reactor is preheated to remove any residual moisture. L-lactide (400 g), 3,6-Di-(n-butyl)-1,4-dioxane-2,5-dione (40 g), 0.44 mL dodecanol (initiator), 1 L toluene and 1.2 mL stannous octoate are charged to the reactor and the mixture is heated to 120° C. with stirring and held there for 24 hrs. The reaction mixture is cooled and one liter of chloroform is added to the reactor to dilute the solution. The solution is then poured into 6 L of methanol wherein the product precipitates. The product is filtered, washed with methanol and dried at 80° C. under vacuum to a constant weight.

Example 3

Stent Fabricated from above Block or Random Copolymer

A single screw extruder is used to fabricate tubes of the polymers. The extruder is heated to 420° C. and tubing with a designated ID of 0.021 in. and OD of 0.064 in. is extruded. The extruded tubing is radially expanded 400% and axially 20% to afford an expanded tubing having an ID of 0.124 in. and an OD of 0.136 in. Stents are then cut from the tubing using a green femto- or pico-second laser and the stents so fabricated are crimped down to ID 0.53 in. and then sterilized.

What is claimed is:

1. A stent comprising:
a stent body that is fabricated of a composition, coated with one or more layers of the composition, or both, the composition comprising:
about 1 to about 5 wt % poly[L-lactide-co-(3,6-dialkyl-1,4-dioxane-2,5-dione)] as a blend with
about 75 to about 90 wt % poly(L-lactide) and
about 9 to about 20 wt % poly(3,6-dialkyl-1,4-dioxane-2,5-dione), wherein:
the poly[L-lactide-co-(3,6-dialkyl-1,4-dioxane-2,5-dione)] is a random or a block copolymer;
the poly[L-lactide-co-(3,6-dialkyl-1,4-dioxane-2,5-dione)] is about 10 to 50 mol % 3,6-dialkyl-1,4-dioxane-2,5-dione-derived constitutional unit;
the alkyl groups of the poly[L-lactide-co-(3,6-dialkyl-1,4-dioxane-2,5-dione)] are the same; those like alkyl groups are the same as or different from the alkyl groups of the poly(3,6-dialkyl-1,4-dioxane-2,5-dione), which alkyl groups are likewise the same; and
the alkyl groups are selected from the group consisting of 2C-20C straight or branched chain alkyl and 3C-6C cycloalkyl.

2. The stent of claim 1, wherein the alkyl group is selected from the group consisting of 2C-6C straight or branched chain alkyl.

3. The stent of claim 1, wherein the poly[L-lactide-co-(3,6-dialkyl-1,4-dioxane-2,5-dione)] is a random copolymer.

4. The stent of claim 1, wherein the poly[L-lactide-co-(3,6-dialkyl-1,4-dioxane-2,5-dione)] is a block copolymer.

5. The stent of claim 4, wherein the block copolymer is a diblock copolymer.

6. The stent of claim, 4, wherein the block copolymer is a triblock copolymer in which poly(L-lactide) is the middle block between two poly(3,6-dialkyl-1,4-dioxane-2,5-dione) blocks.

7. The stent of claim 1, wherein one or more of the polymers of the composition is a star polymer.

8. The stent of claim 7, wherein the star polymer(s) is(are) independently regular or variegated.

9. The stent of claim 8, wherein the initiator(s) of star polymer polymerization is, or are independently, selected from the group consisting of 1,3-dihydroxy-2-hydroxymethylpropane, pentaerythritol and cyclopropane-1,2,3-tricarboxylic acid.

10. The stent of any one of claim 1, 4, 5, or 6, wherein the composition comprises poly[L-lactide-co-(3,6-dialkyl-1,4-dioxane-2,5-dione)] block copolymer wherein the lactide block(s) have a number average molecular weight of about 100 to 300 Kg/mol and the 3,6-dialkyl-1,4-dioxane-2,5-dione block(s) have a number average molecular weight of about 10 to 30 Kg/mol.

11. The stent of claim 10, wherein the poly[L-lactide-co-(3,6-dialkyl-1,4-dioxane-2,5-dione)] has a number average molecular weight of about 110 to about 1,000 Kg/mol.

12. The stent of claim 1, wherein the device body is fabricated from the composition.

13. The stent of claim 12, wherein the device body is coated with one or more layers, one or more of which comprises the composition.

14. The stent of claim 13, wherein one or more of the layers comprises a therapeutic agent.

15. The stent of claim 1, wherein the device body is comprised of different material(s) than the composition.

16. The stent of claim 15, wherein the device body is coated with one or more layers, one or more of which comprises the composition.

17. The stent of claim 16, wherein one or more of the layers comprises a therapeutic agent.

* * * * *